(12) United States Patent
Rezach

(10) Patent No.: US 8,764,804 B2
(45) Date of Patent: Jul. 1, 2014

(54) BONE FASTENER AND METHODS OF USE

(75) Inventor: William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 191 days.

(21) Appl. No.: 13/360,276

(22) Filed: Jan. 27, 2012

(65) Prior Publication Data

US 2013/0197593 A1    Aug. 1, 2013

(51) Int. Cl.
*A61B 17/70*      (2006.01)
(52) U.S. Cl.
USPC .......................................... 606/267; 606/266
(58) Field of Classification Search
USPC ......................................... 606/264, 265, 267
See application file for complete search history.

(56) References Cited

U.S. PATENT DOCUMENTS

| 7,993,372 B2 * | 8/2011 | Winslow et al. | 606/246 |
| 2005/0187549 A1 * | 8/2005 | Jackson | 606/61 |
| 2010/0234891 A1 * | 9/2010 | Freeman et al. | 606/266 |

* cited by examiner

*Primary Examiner* — Andrew Yang

(57) ABSTRACT

A bone fastener comprises a proximal portion including an inner surface that defines a cavity. A carrier is disposed in fixed engagement with the inner surface and includes at least one arm defining a proximal face. A pivoting member is disposed with the carrier. The pivoting member defines an implant cavity with the proximal portion. A distal portion defines a longitudinal axis and is configured to penetrate tissue. The bone fastener further includes a first coupling member. The proximal portion is rotatable relative to the distal portion in a first plane of a body and the pivoting member is rotatable relative to the proximal portion in a second plane. The first coupling member is engageable with the proximal face such that the carrier engages the distal portion to fix the bone fastener in an orientation. Methods of use are disclosed.

20 Claims, 9 Drawing Sheets

BONE FASTENER AND METHODS OF USE

TECHNICAL FIELD

The present disclosure generally relates to medical devices for the treatment of spinal disorders, and more particularly to a spinal implant system including a bone fastener that provides stabilization while reducing stress on spinal elements.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. During surgical treatment, one or more rods may be attached via fasteners to the exterior of two or more vertebral members to provide stability to a treated region. This disclosure describes an improvement over these prior art technologies.

SUMMARY

Accordingly, a spinal implant system is provided. In one embodiment, in accordance with the principles of the present disclosure, a bone fastener is provided. The bone fastener comprises a proximal portion including an inner surface that defines a cavity. A carrier is disposed in fixed engagement with the inner surface and includes at least one arm defining a proximal face. A pivoting member is disposed with the carrier and is relatively moveable therefrom. The pivoting member defines an implant cavity with the proximal portion. A distal portion defines a longitudinal axis and is configured to penetrate tissue. The bone fastener further includes a first coupling member. The proximal portion is rotatable relative to the distal portion in a first plane of a body and the pivoting member is rotatable relative to the proximal portion in a second plane of the body. The first coupling member is engageable with the proximal face such that the carrier engages the distal portion to fix the bone fastener in an orientation.

In one embodiment, a spinal implant system is provided. The spinal implant system comprises at least one bone fastener comprising a receiver defining a first longitudinal axis and including spaced apart arms that include an inner surface of the receiver. The receiver includes an extension. A carrier extends between a first end and a second end and includes a first surface disposed in fixed engagement with the inner surface. The carrier includes a second concave surface that defines a first lateral opening and a second lateral opening, and a pair of spaced apart arms each defining a proximal face. A saddle defines a first surface configured for slidable engagement with the second surface of the carrier along an arcuate path and a second concave surface that defines an implant cavity with the receiver. The implant cavity defines a second axis transverse to the first longitudinal axis and is configured for disposal of an implant. The saddle includes a first arm that extends through the first lateral opening and a second arm that extends through the second lateral opening. The first and second arms of the saddle are engageable with the carrier to limit movement of the saddle. A tissue penetrating shaft extends between a first end and a second end. The first end includes a cavity configured for disposal of the extension. A first setscrew is rotatable relative to the receiver and engageable with the inner surface for axial translation relative to the receiver. The first setscrew includes a distal face configured to engage the proximal face of the carrier and an inner surface that defines a longitudinal passageway. A second setscrew includes a tip and is rotatable relative to the first setscrew and engageable with the inner surface of the first setscrew for axial translation relative to the first setscrew. A vertebral rod is configured for disposal within the implant cavity. The bone fastener is movable between a first configuration such that the receiver is selectively rotatable relative to the shaft in a transverse plane of a body and the saddle is selectively rotatable relative to the receiver in a sagittal plane of the body, and a second configuration such that the first setscrew is rotatable to advance the distal face into engagement with the proximal face of each of the pair of spaced apart arms such that the carrier applies a first force and engages the shaft and the second setscrew is rotatable to advance the tip into engagement with the rod and the rod engages the concave surface of the saddle to apply a second force to the shaft through the carrier. The application of the forces and engagement of the carrier with the shaft fixes the bone fastener in an orientation.

In one embodiment, a method for treating a spine disorder is provided. The method comprises the steps of providing a bone fastener comprising: a proximal portion including an inner surface that defines a cavity, a carrier disposed in fixed engagement with the inner surface and including at least one arm defining a proximal face, a pivoting member being disposed with the carrier and relatively moveable therefrom, the pivoting member defining an implant cavity with the proximal portion, a distal portion defining a longitudinal axis and being configured to penetrate tissue and a first coupling member; attaching the distal portion with vertebrae; providing a vertebral rod disposed in an orientation; selectively rotating the proximal portion relative to the distal portion in a first plane of a body and selectively rotating the pivoting member relative to the proximal portion in a second plane of the body to the orientation to dispose the rod in the implant cavity; and engaging the first coupling member with the proximal face such that the carrier engages the distal portion to prevent movement of the proximal portion relative to the distal portion.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
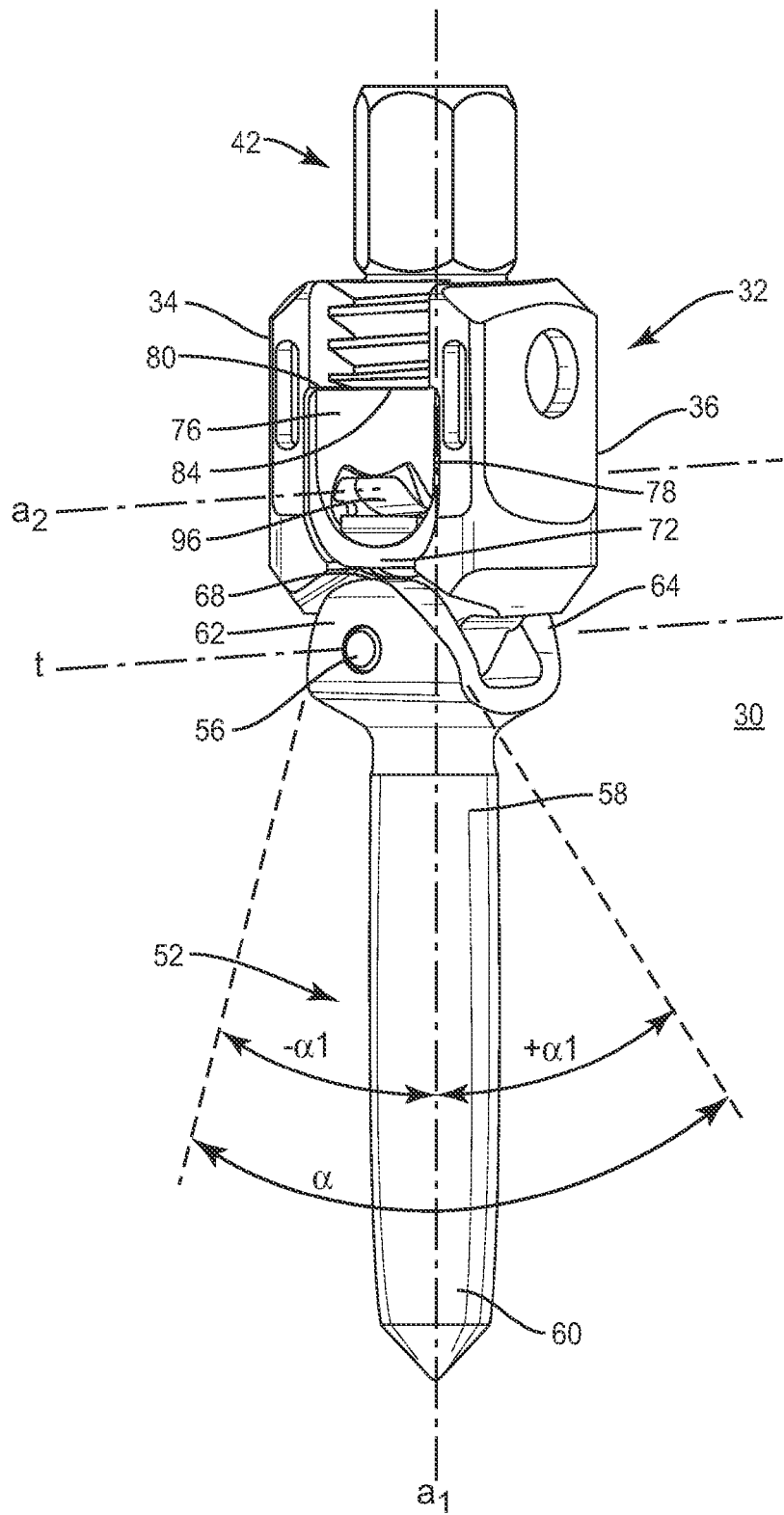
FIG. 1 is a perspective view of one embodiment of a bone fastener of a system in accordance with the principles of the present disclosure.
Figure 2:
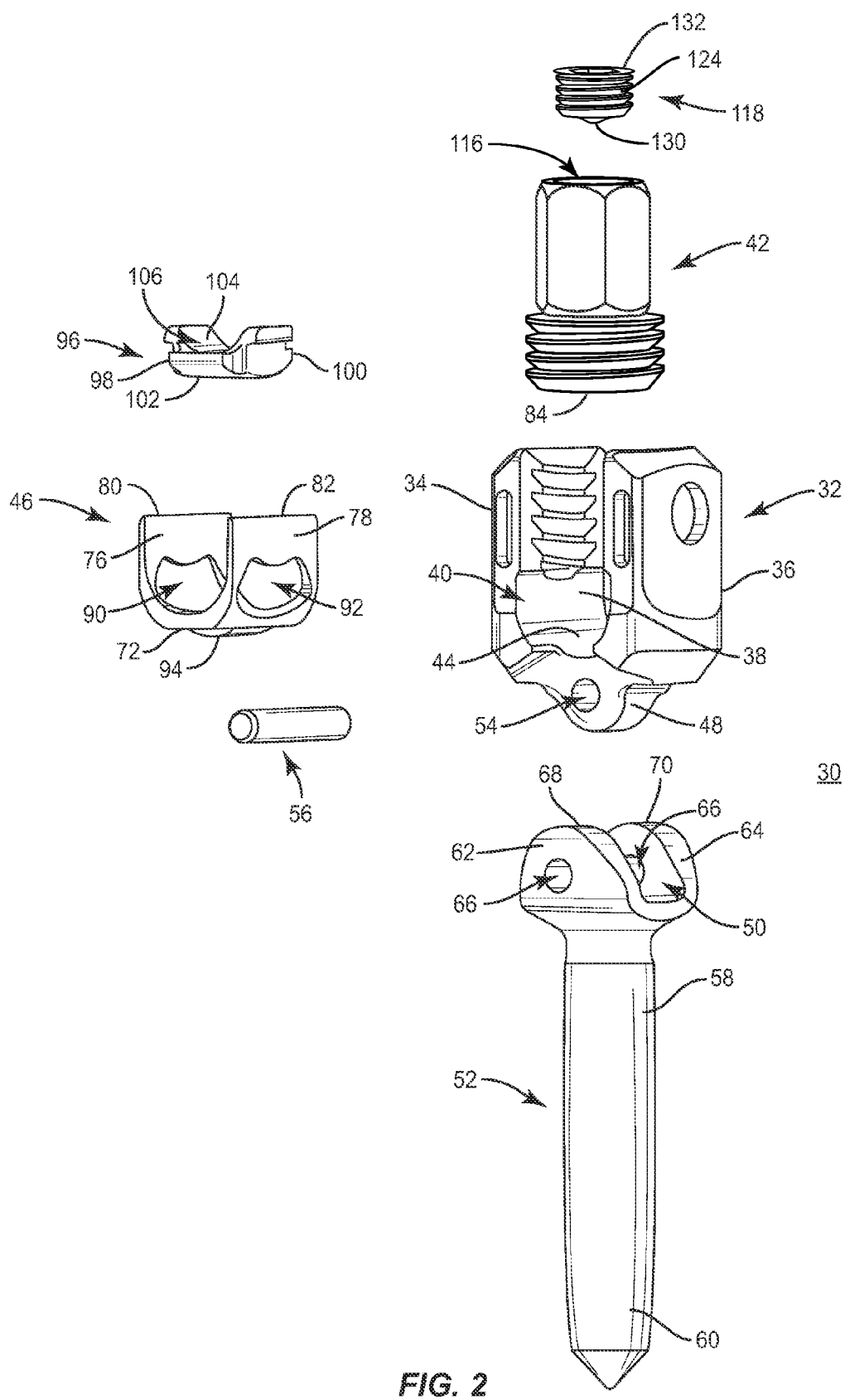
FIG. 2 is a perspective view of the bone fastener shown in FIG. 1 with parts separated.

The exemplary embodiments of a surgical system and methods of use disclosed are discussed in terms of medical devices for the treatment of spinal disorders and more particularly, in terms of a spinal implant system including a bone fastener that provides stabilization while reducing stress on spinal elements.

In one embodiment, the spinal implant system includes a transverse sagittal angulating and accommodating screw. The screw provides direct control of an implant. In one embodiment, this configuration allows sagittal accommodation to a spinal rod. It is envisioned that this configuration allows for sagittal manipulation once a spinal rod has been placed into the screw. It is further envisioned that the screw allows a head of the screw to pivot in a transverse plane of a body of a patient. It is contemplated that the screw may have a pivoting head combined with a pivoting saddle and may lock in the transverse plane to allow sagittal accommodation to a spinal rod and sagittal manipulation once a spinal rod has been positioned within the head of the screw.

In one embodiment, the bone fastener provides independent transverse and sagittal movement that allows a surgeon to achieve more control during correction, which provides more precise correction. In one embodiment, the bone fastener includes a saddle that pivots approximately in a range of 26° in a sagittal plane. It is contemplated that such range can be measured +/−13° from an axis. In one embodiment, the bone fastener includes a head that pivots approximately in a range of 60° in a transverse plane. It is contemplated that such range can be measured +/−30° from an axis.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur (prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal implant system including a bone fastener, related components and exemplary methods of employing the bone fastener in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of a spinal implant system including a bone fastener 30 in accordance with the principles of the present disclosure.

The components of the spinal implant system can be fabricated from biologically acceptable materials suitable for medical applications, including metals, synthetic polymers, ceramics and bone material and/or their composites, depending on the particular application and/or preference of a medical practitioner. For example, the components of bone fastener 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the spinal implant system may have material composites, including the above materials, to achieve various desired characteristics such as strength, rigidity, elasticity, compliance, biomechanical performance, durability and radiolucency or imaging preference. The components of the spinal implant system, individually or collectively, may also be fabricated from a heterogeneous material such as a combination of two or more of the above-described materials. The components of the spinal implant system may be monolithically formed, integrally connected or include fastening elements and/or instruments, as described herein.

Bone fastener 30 comprises a proximal portion, such as, for example, a receiver 32 defining a first longitudinal axis $a_1$ and including spaced apart arms 34, 36 extending parallel to first longitudinal axis $a_1$. Receiver 32 includes an inner surface 38. It is contemplated that arm 34 and/or arm 36 may be disposed at alternate orientations, relative to first longitudinal axis $a_1$, such as, for example, transverse, perpendicular and/or other angular orientations such as acute or obtuse, co-axial and/or may be offset or staggered. Arms 34, 36 each include an arcuate outer surface. It is envisioned that the outer surfaces of arms 34, 36 may include a recess or cavity configured to receive an insertion tool, compression instrument and/or instruments for inserting and tensioning bone fastener 30.

Inner surface 38 of receiver 32 defines a U-shaped cavity 40 extending between arms 34, 36. It is envisioned that all or only a portion of cavity 40 may have alternate cross section configurations, such as, for example, oval, oblong, triangular, square, polygonal, irregular, uniform, non-uniform, offset, staggered, and/or tapered. At least a portion of inner surface 38 is threaded and engageable with a first coupling member, such as, for example, a first setscrew 42. It is envisioned that inner surface 38 can include a thread form located adjacent arm 34 and a thread form located adjacent arm 36 each configured for engagement with first setscrew 42, as will be described. It is envisioned that inner surface 38 may be disposed with first setscrew 42 in alternate fixation configurations, such as, for example, friction fit, pressure fit, locking protrusion/recess, locking keyway and/or adhesive. It is contemplated that all or only a portion of inner surface 38 may have alternate surface configurations to enhance fixation with the setscrew such as, for example, rough, arcuate, undulating, mesh, porous, semi-porous, dimpled and/or textured according to the requirements of a particular application.

Inner surface 38 of receiver 32 defines a concave surface 44 adjacent a base portion thereof and being configured to receive at least a portion of a carrier 46, described below, to retain carrier 46 with receiver 32. Concave surface 44 extends distally and is recessed from inner surface 38. It is envisioned that concave surface 44 may be disposed in the center of inner surface 38 such that concave surface 44 is equidistant from arm 34 and arm 36. It is further envisioned that concave surface 44 may also be offset such that concave surface 44 is disposed closer to arm 34 than arm 36, or vice versa. It is contemplated that concave surface 44 can extend into inner surface 38 without extending through a bottom surface of receiver 32. Concave surface 44 is configured to receive a corresponding convexly curved portion of carrier 46. It is contemplated that all or only a portion of concave surface 44 may be variously configured and dimensioned, such as, for example, oval, oblong, square, rectangular, polygonal, irregular, uniform, non-uniform, offset, staggered, tapered, consistent or variable, depending on the requirements of a particular application.

Receiver 32 includes an arcuate extension 48 extending distally from a distal end of receiver 32 between arms 34, 36. Extension 48 is configured for disposal in a cavity 50 in a distal portion, such as, for example, a tissue penetrating shaft 52 of bone fastener 30. It is envisioned that all or only a portion of extension 48 may be variously configured and dimensioned, such as, for example, planar, concave, polygonal, irregular, uniform, non-uniform, staggered, tapered, consistent or variable, depending on the requirements of a particular application.

Extension 48 includes an inner surface that defines a cavity, such as, for example, a first channel 54 extending therethrough along a transverse axis t of bone fastener 30 relative to first longitudinal axis $a_1$ so as to form a passageway configured to receive a transverse pin 56 to retain receiver 32 with shaft 52 of bone fastener 30. It is contemplated that first channel 54 may extend through extension 48 in various orientations relative to first longitudinal axis $a_1$, such as, for example, perpendicular and/or other angular orientations such as acute or obtuse and/or may be offset or staggered. First channel 54 has a tubular configuration for receiving cylindrical pin 56. It is envisioned. that all or only a portion of first channel 54 may be variously configured and dimensioned, such as, for example, oval, oblong, square, rectangular, polygonal, irregular, uniform, non-uniform, offset, staggered, tapered, consistent or variable, depending on the requirements of a particular application.

Shaft 52 extends between a first end 58 and a second end 60 along first longitudinal axis $a_1$. Shaft 52 has a cylindrical cross section configuration that extends to a pointed distal tip. It is contemplated that shaft 52 may include an outer surface having an external threaded form. It is contemplated that the thread form on the outer surface of shaft 52 may include a single thread turn or a plurality of discrete threads. It is further contemplated that other engaging structures may be located on shaft 52, such as, for example, a nail configuration, barbs, expanding elements, raised elements and/or spikes to facilitate engagement of shaft 52 with tissue, such as, for example, vertebrae.

It is envisioned that all or only a portion of shaft 52 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 52 may include one or a plurality of openings. It is contemplated that all or only a portion of the outer surface of shaft 52 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 52 may be disposed at alternate orientations, relative to first longitudinal axis $a_1$, such as, for example, transverse, perpendicular and/or other angular orientations such as acute or obtuse, co-axial and/or may be offset or staggered. It is further envisioned that all or only a portion of shaft 52 may be cannulated.

Shaft 52 includes a pair of convexly curved spaced apart arms 62, 64 extending proximally from first end 58 defining cavity 50. It is envisioned that at least a portion of arms 62, 64 may also be concavely curved or planar, according to the requirements of a particular application. Cavity 50 is substantially U-shaped and is configured for disposal of extension 48. The shape of cavity 50 is defined by planar inner surfaces of arms 62, 64 and a planar proximal face of first end 58, which is transverse to the planar inner surfaces of arms 62, 64 such that cavity 50 has a planar bottom wall and planar side walls extending transversely from either end of the planar bottom wall. It is envisioned that all or only a portion of cavity 50 may have alternate cross section configurations, such as, for example, oval, oblong, triangular, square, polygonal, irregular, uniform, non-uniform, offset, staggered, and/or tapered.

First end 58 of shaft 52 includes an inner surface that defines a second channel 66 extending through each of arms 62, 64 and cavity 50 transverse to first longitudinal axis $a_1$ so as to form a passageway configured to receive transverse pin 56 to retain receiver 32 with shaft 52. It is contemplated that second channel 66 may extend through arms 62, 64 in other orientations relative to first longitudinal axis $a_1$, such as, for example, perpendicular and/or other angular orientations such as acute or obtuse and/or may be offset or staggered. Second channel 66 has a tubular configuration for receiving pin 56. It is envisioned that all or only a portion of second channel 66 may be variously configured and dimensioned, such as, for example, oval, oblong, square, rectangular, polygonal, irregular, uniform, non-uniform, offset, staggered, tapered, consistent or variable, depending on the requirements of a particular application. Second channel 66 has a diameter that is approximately the same as a diameter of first channel 54 of extension 48. Transverse pin 56 has a diameter that is less than that of first and second channels 54, 66 such that pin 56 may be received within first and second channels 54, 66.

To engage receiver 32 with shaft 52, extension 48 of receiver 32 is inserted into cavity 50 of shaft 52 such that channels 54, 66 are aligned. Transverse pin 56 is inserted through channels 54, 66 such that pin 56 engages at least a portion of receiver 32 and shaft 52 to connect receiver 32 with shaft 52. Receiver 32 is selectively rotatable relative to shaft 52 within a first plane, such as, for example, a transverse plane TP (FIG. 8) of a body of a patient.

Figure 3:
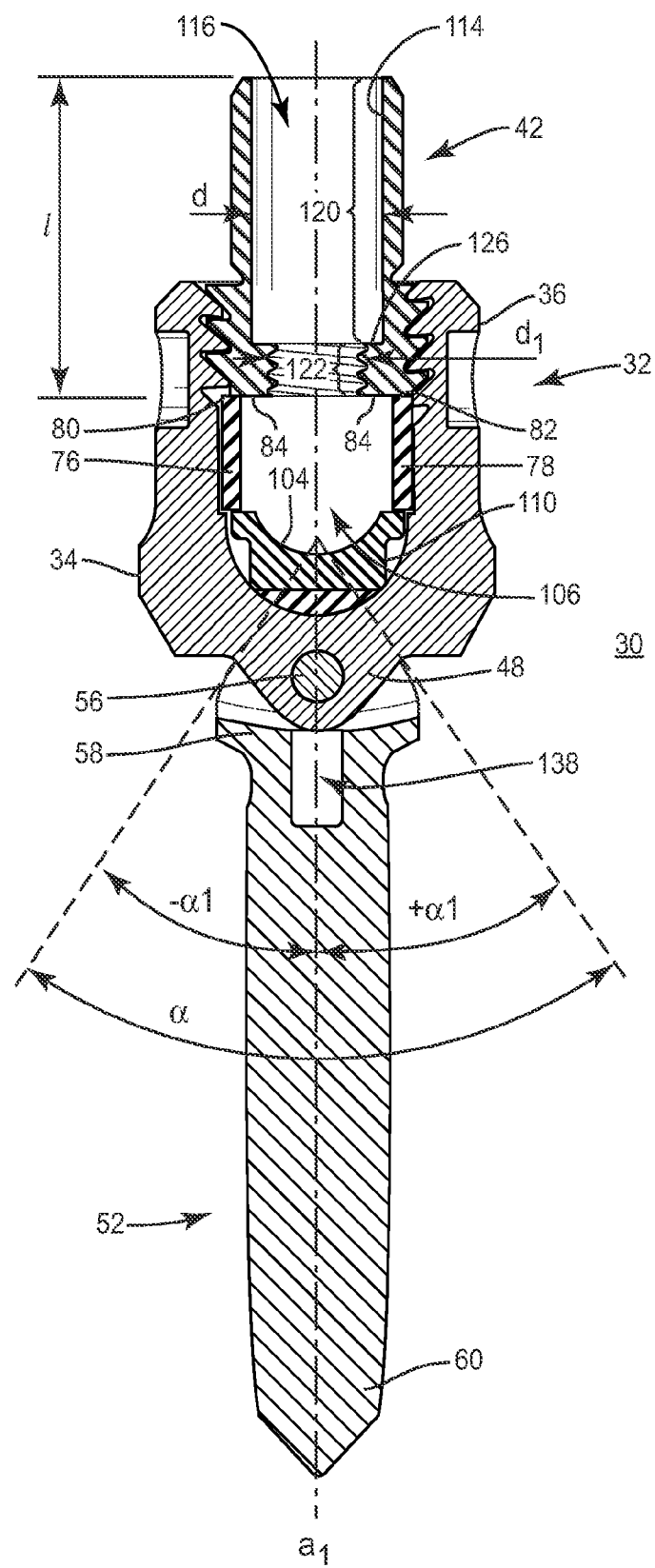
FIG. 3 is a side view, in cross section, of the bone fastener shown in FIG. 1.
Figure 4:
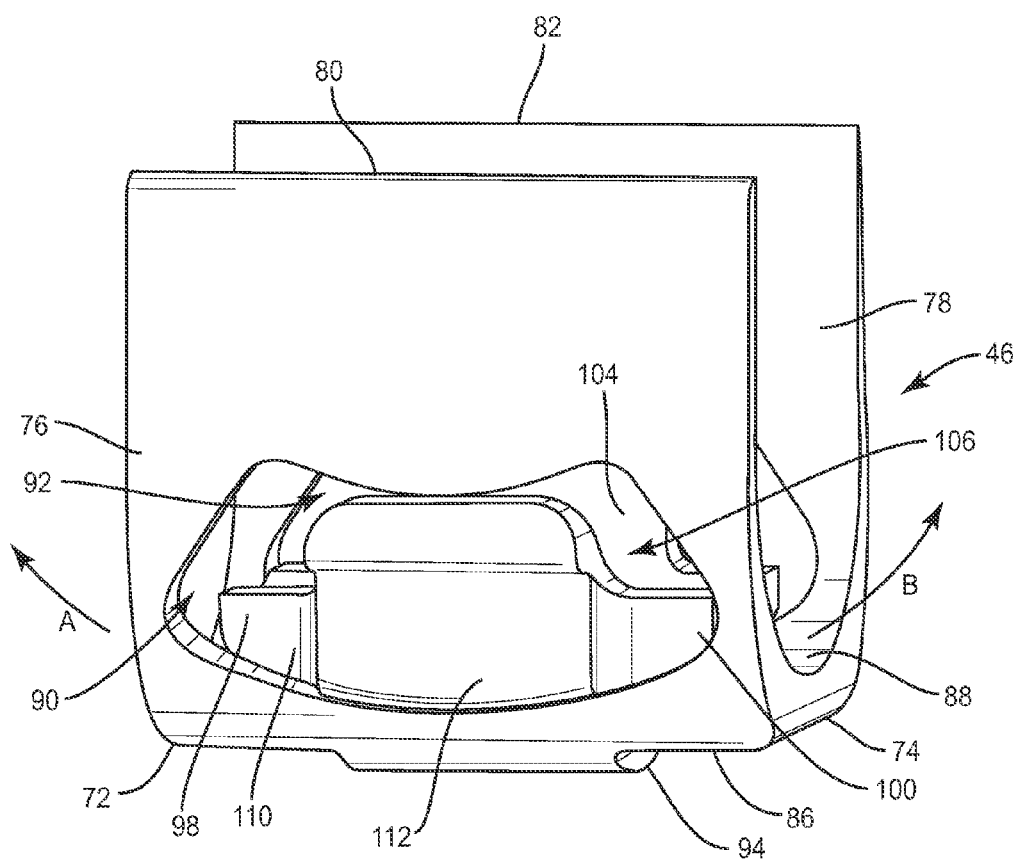
FIG. 4 is a perspective view of components of the bone fastener shown in FIG. 1.

Receiver 32 and shaft 52 are relatively rotatable about transverse axis t, for example, such that shaft 52 is rotatable relative to receiver 32 through an angular range α (FIGS. 1 and 3). Shaft 52 is pivotable through angular range α at +/−an angle α1 relative to axis $a_1$. It is contemplated that angular range α may include a range of approximately 0 to 60 degrees. It is further contemplated that angle α1 may include a range of approximately +/−30 degrees.

Figure 7:
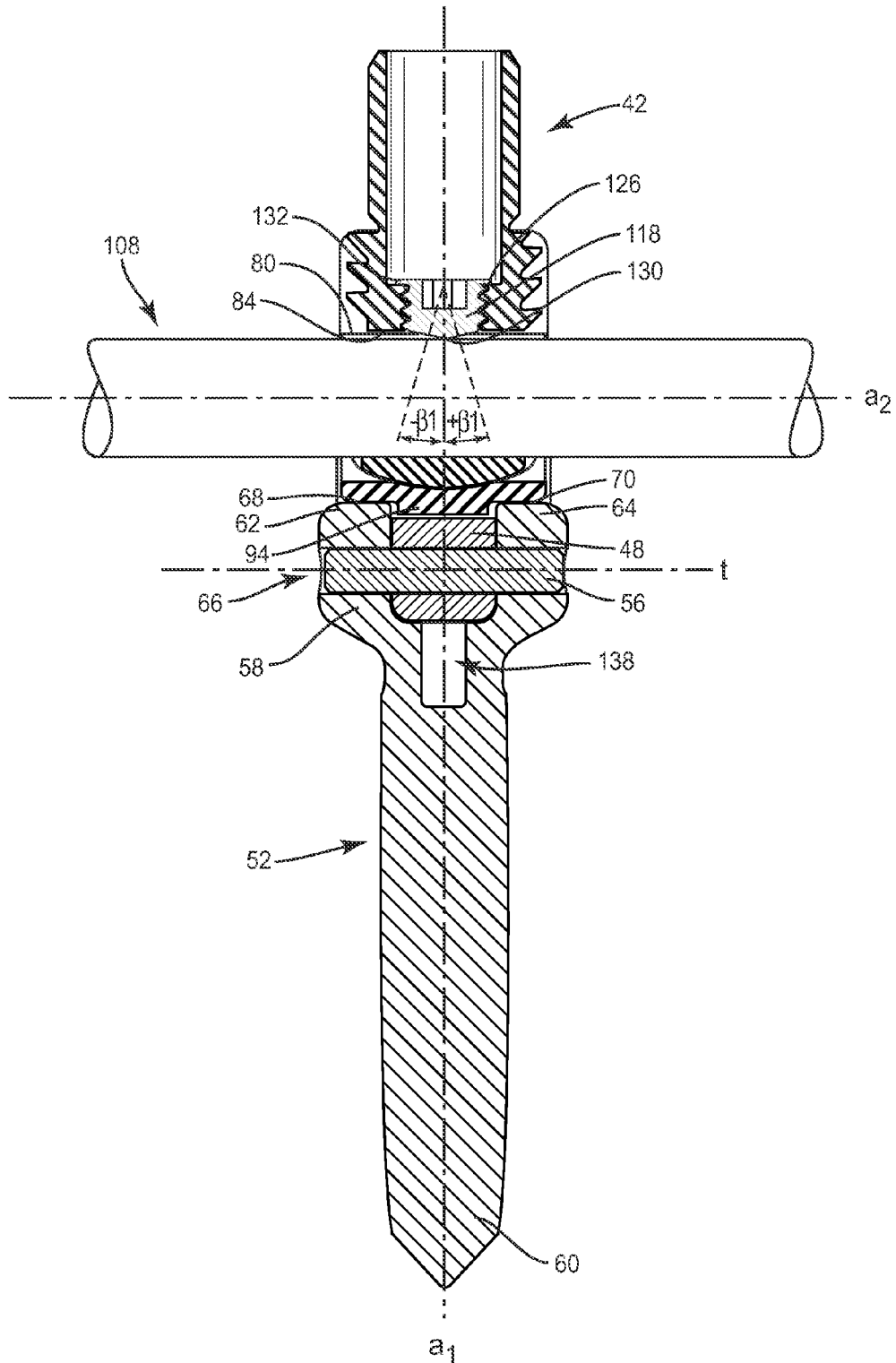
FIG. 7 is a side view, in cross section, of one embodiment of a bone fastener of a system in accordance with the principles of the present disclosure.

Pin 56 is beveled at either end, as shown in FIG. 7, to facilitate insertion of pin 56 into channels 54, 66. It is contemplated that receiver 32 may be disposed with shaft 52 for relative movement in orientations relative to first longitudinal axis $a_1$, such as, for example, transverse, perpendicular and/or other angular orientations such as acute or obtuse, co-axial and/or may be offset or staggered. It is further contemplated that receiver 32 may move relative to shaft 52 in alternate planes relative to a body, such as, for example, vertical, horizontal, diagonal, transverse, coronal and/or sagittal planes of a body. It is envisioned that receiver 32 may be retained with shaft 52 in alternate fixation configurations, such as, for example, friction fit, pressure fit, locking protrusion/recess, locking keyway and/or adhesive.

Arms 62, 64 include convexly curved interference surfaces 68, 70 disposed along an exterior surface thereof configured to engage corresponding interference surfaces 72, 74 on carrier 46 to prevent receiver 32 from moving relative to shaft 52 upon fixation within an orientation of bone fastener 30, as will be described. It is envisioned that interference surfaces 68, 70 may also be concavely curved, irregular or planar, according to the requirements of a particular application. It is further envisioned that all or only a portion of interference surfaces 68, 70 may have alternate surface configurations to enhance fixation with carrier 46 such as, for example, rough, arcuate, undulating, mesh, porous, semi-porous, dimpled and/or textured according to the requirements of a particular application.

Carrier 46 is defined by at least one arm, such as, for example, opposing arms 76, 78. Arm 76 includes a planar proximal face 80 and arm 78 includes a planar proximal face 82. Arms 76, 78 are elongated and extend in a substantially parallel orientation such that proximal faces 80, 82 are configured to engage a distal face 84 of first setscrew 42 such that carrier 46 applies a first force and engages shaft 52 to prevent receiver 32 from moving relative to shaft 52, as will be described.

Carrier 46 includes a first surface 86 configured for fixed engagement with inner surface 38 of receiver 32 and a second concave surface 88 defining a first lateral opening 90 in arm 76 and a second lateral opening 92 in arm 78. First surface 86 includes a projection 94 extending distally therefrom along first longitudinal axis $a_1$ and being configured for receipt within concave surface 44. This configuration retains carrier 46 with receiver 32 and prevents movement of carrier 46 within cavity 40 of receiver 32. Projection 94 is centrally disposed with carrier 46. It is envisioned that projection 94 may also be offset. It is envisioned that receiver 32 may be retained with carrier 46 in alternate fixation configurations, such as, for example, friction fit, pressure fit, locking protrusion/recess, locking keyway and/or adhesive.

Figure 5:
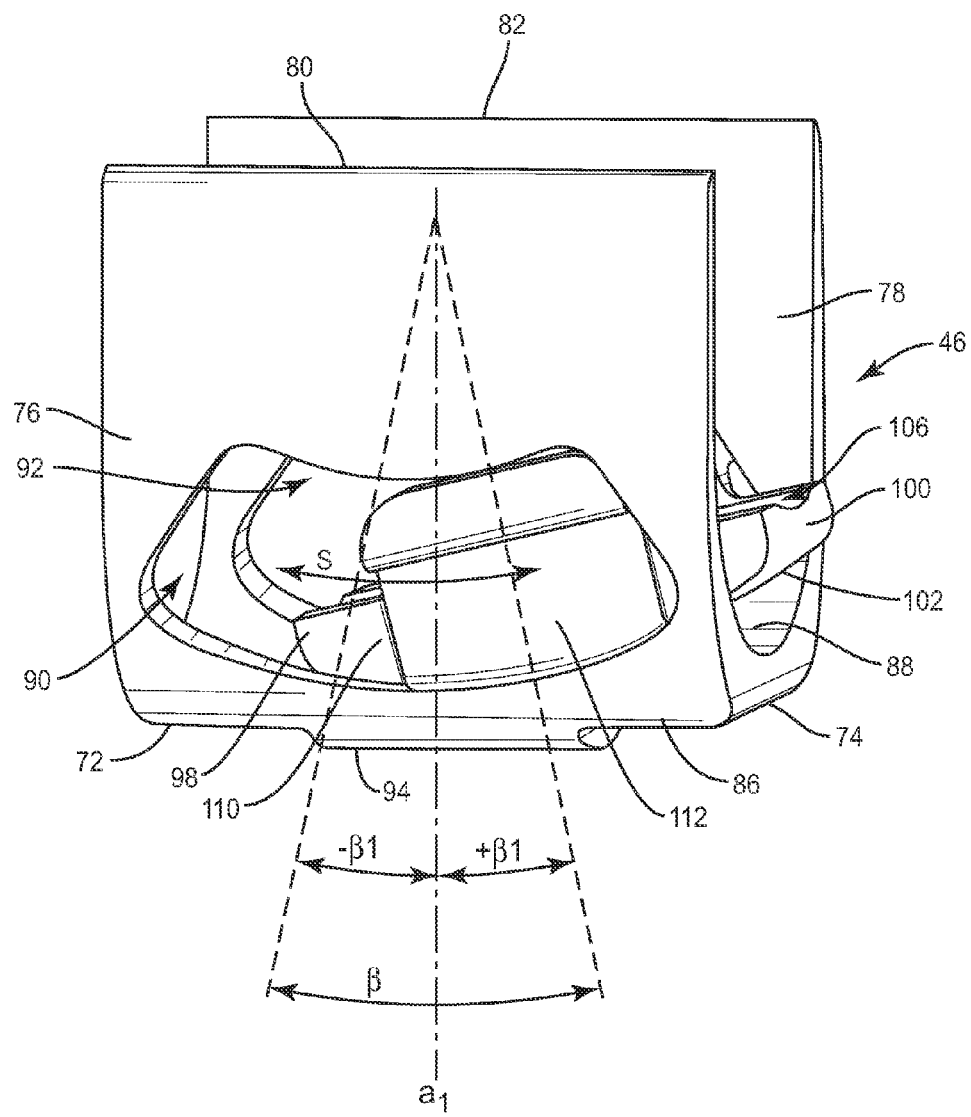
FIG. 5 is a perspective view of components of the bone fastener shown in FIG. 1.
Figure 6:
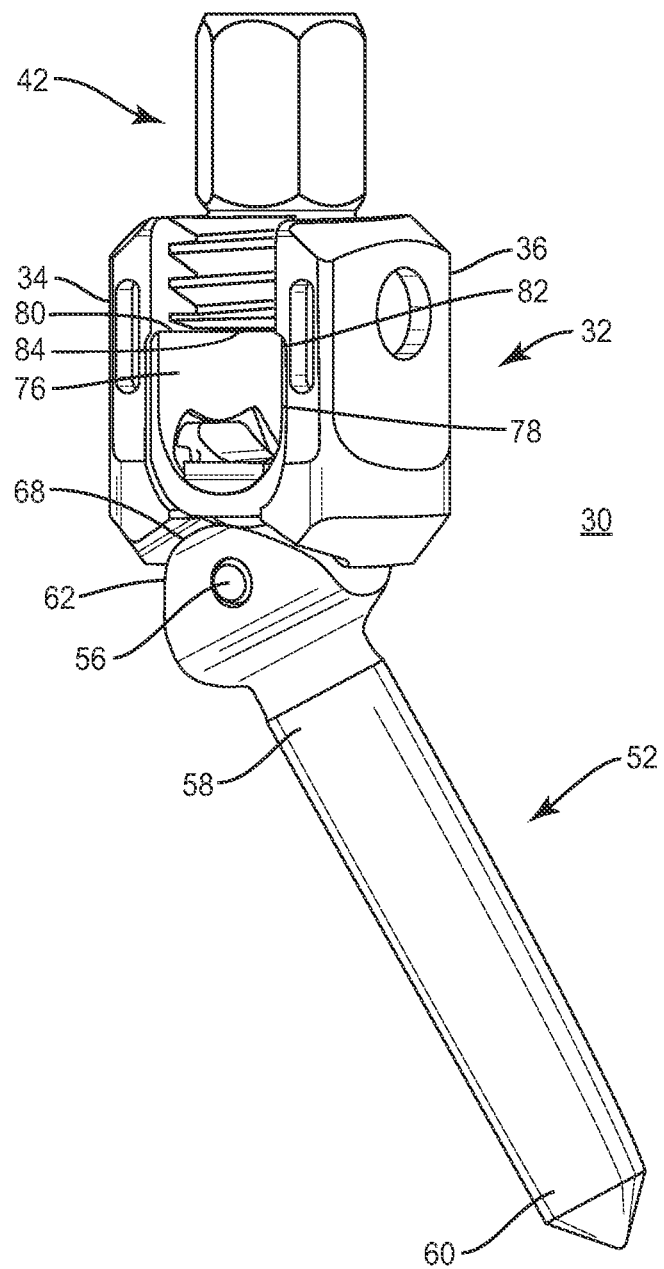
FIG. 6 is a perspective view of components of the bone fastener shown in FIG. 1.

Second surface 88 of carrier 46 is configured for disposal of a pivoting member, such as, for example, a saddle 96, described below. First and second lateral openings 90, 92 each include concavely curved top and bottom surfaces extending between planar side surfaces so as to define an arcuate path S, as shown in FIG. 5. The side surfaces of first and second lateral openings 90, 92 are disposed at an angle of approximately 45 degrees relative to first longitudinal axis $a_1$. It is contemplated that the side surfaces of first and second lateral openings 90, 92 may be disposed at an angle of approximately 0 to 90 degrees relative to first longitudinal axis $a_1$ and/or may be offset or staggered, or may be disposed at alternate orientations relative to first longitudinal axis $a_1$, such as, for example, transverse, perpendicular and/or other angular orientations such as acute or obtuse, co-axial. First and second lateral openings 90, 92 are disposed in parallel relation. It is contemplated that lateral openings 90, 92 may be disposed at alternate orientations, such as, for example, transverse, and/or other angular orientations such as acute or obtuse, and/or may be offset or staggered.

First and second lateral openings 90, 92 are configured for movement of saddle 96. Saddle 96 is moveable relative to carrier 46 in a first direction, as shown by arrow A in FIG. 4 and a second direction opposite to the first direction, as shown by arrow B. Saddle 96 extends between a first end 98 and a second end 100 and is disposed with carrier 46. Saddle 96 defines a first surface 102 configured for slidable engagement with second surface 88 of carrier 46 along arcuate path S. Saddle 96 defines a second concave surface 104 that defines an implant cavity 106 with receiver 32.

Figure 8:
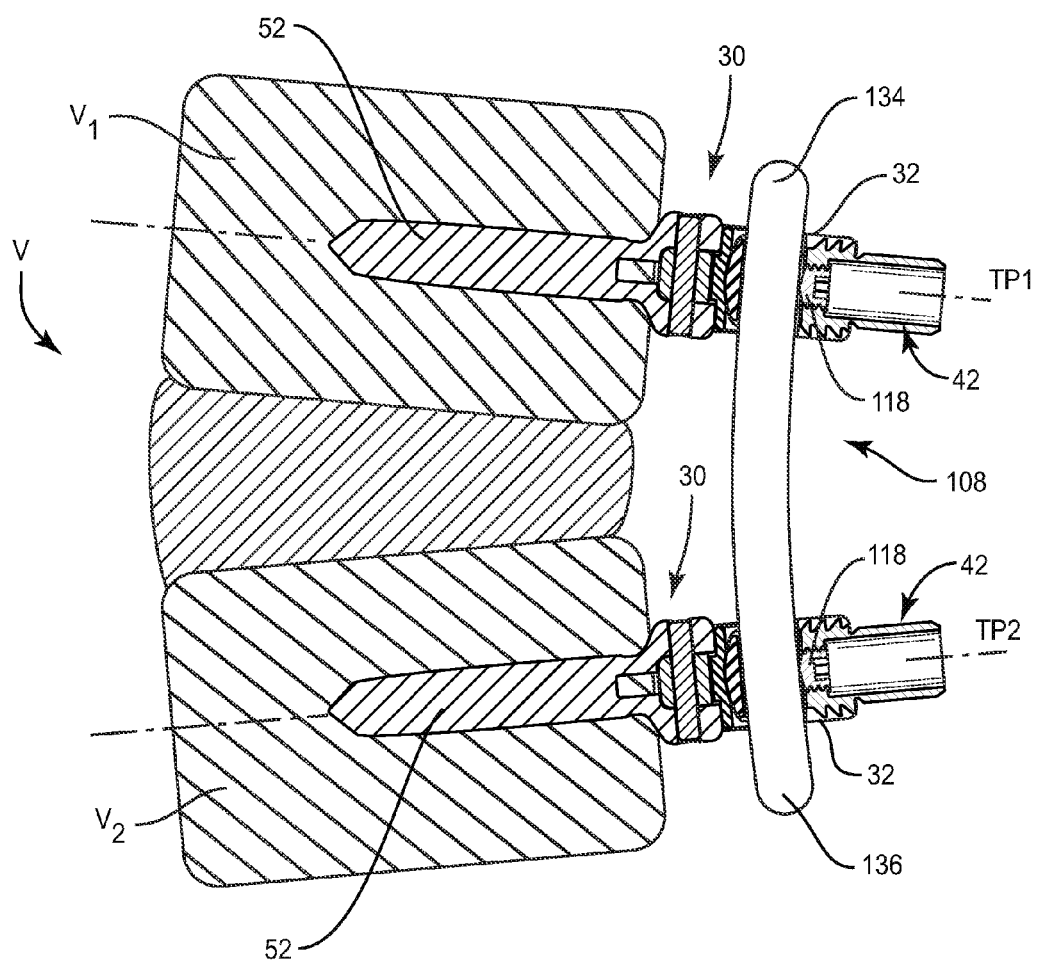
FIG. 8 is side view of a system in accordance with the principles of the present disclosure disposed with vertebrae.
Figure 9:
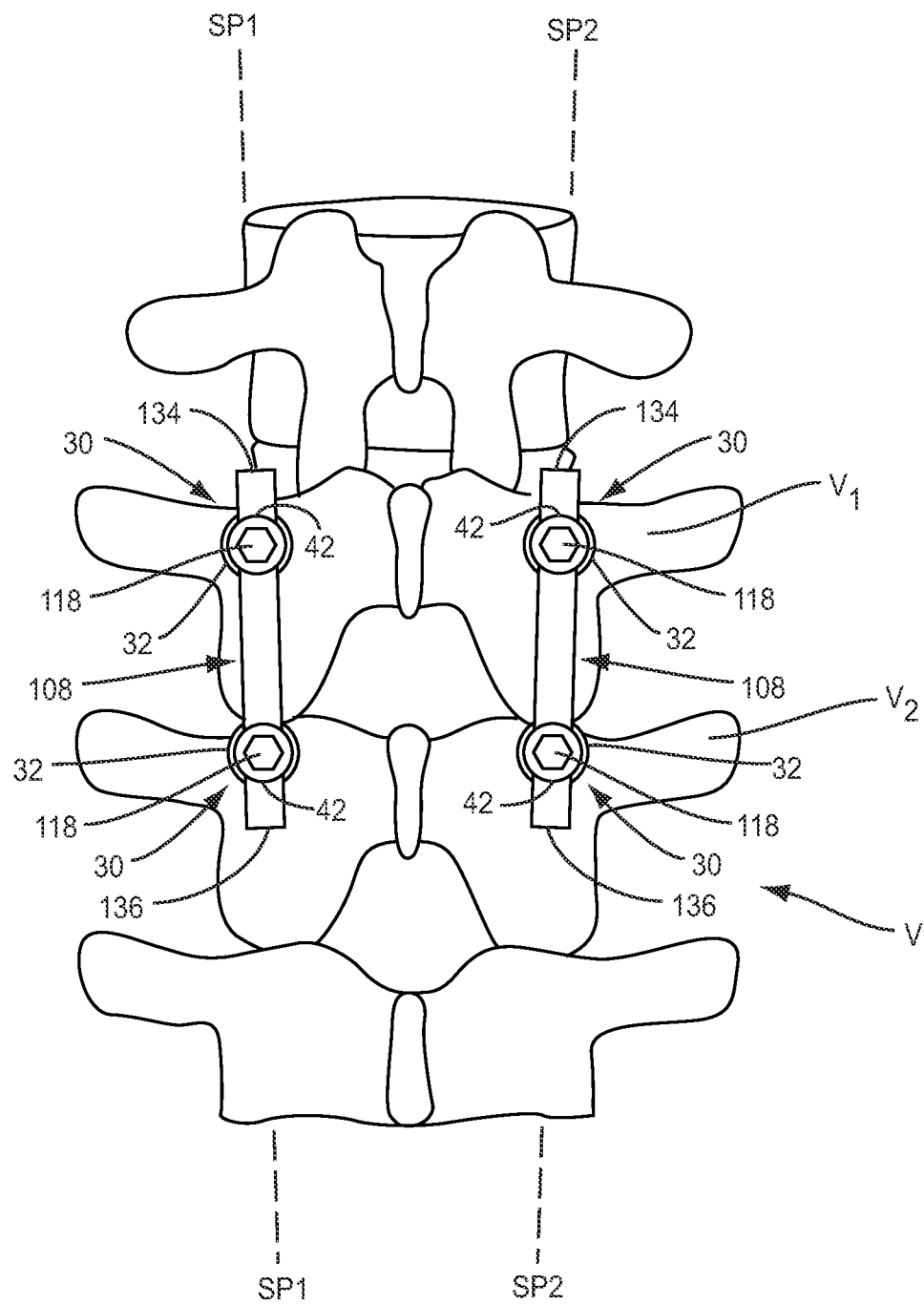
FIG. 9 is a plan view of the system and vertebrae shown in FIG. 8.

Implant cavity 106 defines a second axis $a_2$ transverse to first longitudinal axis $a_1$ and parallel to transverse axis t. Implant cavity 106 is configured to receive and movably support at least a portion of an implant, such as, for example, a vertebral rod 98 (FIGS. 7-9). Rod 108 can translate axially relative to implant cavity 106 along second axis $a_2$ prior to fixation and is pivotable with saddle 96. It is contemplated that at least a portion of rod 108 may be disposed within implant cavity 106 for relative movement in orientations relative to second axis $a_2$, such as, for example, transverse, perpendicular and/or other angular orientations such as acute or obtuse, co-axial and/or may be offset or staggered. It is envisioned that implant cavity 106 may have alternate cross section configurations, such as, for example, oval, oblong, triangular, rectangular, square, polygonal, irregular, uniform, non-uniform, variable and/or tapered.

First surface 102 of saddle 96 is curved between first and second ends 98, 100 for slidable engagement with first and second lateral openings 90, 92 and second surface 88 of carrier 46. Saddle 96 includes a pair of opposite sidewalls 110 and tabs 112 that are configured to extend through lateral openings 90, 92. Saddle 96 translates relative to carrier 46 along arcuate path S as limited by the boundaries defined by lateral openings 90, 92 and their engagement with tabs 112.

It is envisioned that saddle 96 may be elastic and pliable in a configuration to react to forces applied and/or force changes, such as, for example, patient growth, trauma and degeneration, and/or component creep, deformation, damage and degeneration, to maintain the applied force transmitted from an implant positioned in implant cavity 106 substantially constant. It is contemplated that saddle 96 can facilitate maintenance of a holding force on an implant positioned in implant cavity 106 to maintain the holding force relatively constant despite patient growth and changes to bone fastener 30.

Saddle 96 translates relative to carrier 46 along arcuate path S such that saddle 96 is selectively rotatable relative to receiver 32 in a second plane, such as, for example, a sagittal plane SP (FIG. 9) of a body of a patient. Saddle 96 is rotatable about second axis $a_2$ through an angular range β (FIGS. 5 and 7). Saddle 96 is pivotable along arcuate path S in slidable engagement with carrier 46 through angular range β at +/−an angle β1 relative to axis a1. It is contemplated that angular range β may include a range of approximately 0 to 26 degrees. It is further contemplated that angle β1 may include a range of approximately +/−13 degrees.

Interference surfaces 72, 74 of carrier 46 extend beyond cavity 40 of receiver 32 such that interference surfaces 72, 74 overlap interference surfaces 68, 70 of receiver 32 when carrier 46 is retained with receiver 32. Interference surfaces 72, 74 are substantially planar and are configured to engage interference surfaces 68, 70 of receiver 32 to prevent receiver 32 from moving relative to shaft 52 when bone fastener 30 is disposed in a fixed orientation. In one embodiment, first setscrew 42 is engageable with inner surface 38 of receiver 32 for axial translation relative to receiver 32 such that first setscrew 42 is rotatable to advance distal face 84 of first setscrew 42 into engagement with proximal faces 80, 82 of carrier 46 to apply a first force and engage shaft 52. This force transmission causes interference surfaces 72, 74 of carrier 46 to engage interference surfaces 68, 70 of shaft 52 to fix bone fastener 30 in an orientation.

First setscrew 42 includes an external thread form formed circumferentially about an exterior surface of first setscrew 42 configured to mate with the thread forms located adjacent arms 34, 36 of receiver 32 to advance distal face 84 of first setscrew 42 distally along first longitudinal axis $a_1$ such that distal face 84 engages proximal faces 80, 82 of carrier 46, as shown in FIG. 7. First setscrew 42 extends from a proximal end to a distal end along first longitudinal axis $a_1$. It is contemplated that the thread form on first setscrew 42 may include a single thread turn or a plurality of discrete threads. The distal end of first setscrew 42 defines distal face 84. It is envisioned that all or only a portion of distal face 84 may be variously configured and dimensioned, such as, for example, planar, convex, concave, polygonal, irregular, uniform, non-uniform, staggered, tapered, consistent or variable, depending on the requirements of a particular application.

First setscrew 42 includes an inner surface 114 that defines a longitudinal passageway 116 configured for disposal of a second coupling member, such as, for example, a second setscrew 118, described below. Longitudinal passageway 116 includes a proximal portion 120 having a diameter d and a distal portion 122 having a reduced diameter $d_1$. The diameters of proximal and distal portions 120, 122 are continuous throughout the lengths thereof. Inner surface 114 of first setscrew 42 is smooth and continuous along proximal portion 120 such that there are no gaps or protrusions. Inner surface 114 is threaded along distal portion 122 so as to mate with a threaded portion 124 of second setscrew 118 to engage first setscrew 42 with second setscrew 118. It is envisioned that inner surface 114 may be disposed with second setscrew 118 in alternate fixation configurations, such as, for example, friction fit, pressure fit, locking protrusion/recess, locking keyway and/or adhesive. It is contemplated that all or only a portion of inner surface 114 may have alternate surface configurations to enhance fixation with second setscrew 118 such as, for example, rough, arcuate, undulating, mesh, porous, semi-porous, dimpled and/or textured according to the requirements of a particular application. Proximal and distal portions 120, 122 define a ledge 126 at an interface between proximal and distal portions 120, 122 configured to engage a ridge on second setscrew 118 when second setscrew 118 is threaded into inner surface 114 of first setscrew 42 to prevent second setscrew 118 from moving distally out of longitudinal passageway 116 along first longitudinal axis $a_1$.

Second setscrew 118 is configured for coaxial orientation with first setscrew 42 and includes a tip 130 including a lower bearing surface configured to engage an implant, such as, for example, vertebral rod 108 disposed within implant cavity 106. Threaded portion 124 mates with the threads of distal portion 122 to couple first and second setscrews 42, 118. It is envisioned that all or only a portion of threaded portion 124 may be variously configured and dimensioned, such as, for example, oval, oblong, square, rectangular, polygonal, irregular, uniform, non-uniform, offset, staggered, tapered, consistent or variable, depending on the requirements of a particular application. It is also envisioned that second setscrew 118 may be disposed with inner surface 114 of first setscrew 42 in alternate fixation configurations, such as, for example, friction fit, pressure fit, locking protrusion/recess, locking keyway and/or adhesive. It is contemplated that all or only a portion of second setscrew 118 may have alternate surface configurations to enhance fixation with inner surface 114 such as, for example, rough, arcuate, undulating, mesh, porous, semi-porous, dimpled and/or textured according to the requirements of a particular application.

Tip 130 is configured to extend distally into cavity 40 of receiver 42 when second setscrew 118 is engaged with inner surface 114 of first setscrew 42 such that a ridge 132 of second setscrew 118 engages ledge 126 of first setscrew 42. Tip 130 extends to engage an implant disposed within implant cavity 106, as shown in FIG. 7. Tip 130 may be variously configured and dimensioned, such as, for example, convex, concave, polygonal, irregular, uniform, non-uniform, staggered, tapered, consistent or variable, depending on the requirements of a particular application. It is contemplated that all or only a portion of the distal face of tip 130 may have alternate surface configurations to enhance engagement of tip 130 with vertebral rod 108 such as, for example, rough, arcuate, undulating, mesh, porous, semi-porous, dimpled and/or textured according to the requirements of a particular application.

Second setscrew 118 is threadably engageable with first setscrew 42 in rotation to effect axial translation of second setscrew 118 such that rotation of second setscrew 118 advances second setscrew 118 distally along first longitudinal axis $a_1$ and into engagement vertebral rod 108 disposed within implant cavity 106. Ridge 132 engages ledge 126 to prevent second setscrew 118 from moving distally out of longitudinal passageway 116 along first longitudinal axis $a_1$. It is contemplated that second setscrew 118 may include a tool receptacle extending through a proximal face of second setscrew 118 configured to receive a driving tool to apply a rotary driving force to second setscrew 118 to engage second setscrew 118 to the threads of distal portion 122 of first setscrew 42.

In one embodiment, second setscrew 118 is engageable with inner surface 114 of first setscrew 42 for axial translation relative to first setscrew 42 such that second setscrew 118 is rotatable to advance tip 130 of first setscrew 42 into engagement with rod 108 to advance rod 108 distally such that rod 108 engages second concave surface 104 of saddle 96. This configuration causes a compressive force between saddle 96 and carrier 46 thereby locking the orientation of saddle 96 relative to arcuate path S. This configuration also applies a second force to shaft 52 through carrier 46. This force transmission causes interference surfaces 72, 74 of carrier 46 to engage interference surfaces 68, 70 of shaft 52 to fix bone fastener 30 in an orientation.

In assembly, operation and use, a spinal implant system including bone fastener 30, similar to that described above, is employed with a surgical procedure for treatment of a spinal disorder affecting a section of a spine of a patient, as discussed herein. In particular, the spinal implant system is employed with a surgical procedure for treatment of a condition or injury of an affected section of the spine including vertebrae V, as shown in FIGS. 8 and 9. It is contemplated that the spinal implant system including bone fastener 30 is attached to vertebrae V for a surgical arthrodesis procedure, such as fusion, and/or dynamic stabilization application of the affected section of the spine to facilitate healing and therapeutic treatment.

In use, to treat the affected section of the spine, a medical practitioner obtains access to a surgical site including vertebra V in any appropriate manner, such as through incision and retraction of tissues. It is envisioned that the spinal implant system including bone fastener 30 may be used in any existing surgical method or technique including open surgery, mini-open surgery, minimally invasive surgery and percutaneous surgical implantation, whereby the vertebrae V is accessed through a micro-incision, or sleeve that provides a protected passageway to the area. Once access to the surgical site is obtained, the particular surgical procedure is performed for treating the spinal disorder. Bone fastener 30 is then employed to augment the surgical treatment. The spinal implant system including bone fastener 30 and vertebral rod 108 can be delivered or implanted as a pre-assembled device or can be assembled in situ. The spinal implant system may be completely or partially revised, removed or replaced.

Pilot holes are made in vertebrae $V_1$ and $V_2$ for receiving shafts 52 of bone fasteners 30. Shafts 52 of first and second bone fasteners 30 are inserted or otherwise connected to vertebrae $V_1$ and $V_2$ according to the particular requirements of the surgical treatment. A pair of bone fasteners 30 are configured to attach upper sections 134 of rods 108 to vertebra $V_1$ and a pair of bone fastener 30 are configured to attach lower sections 136 of rods 108 to adjacent vertebra $V_2$.

With shafts 52 connected to vertebrae $V_1$ and $V_2$, bone fasteners 30 are moveable between a first configuration and a second configuration. In the first configuration, each receiver 32 is attached with shaft 52 such that receiver 32 is selectively and freely rotatable relative to shaft 52 within transverse planes TP1 and TP2 (FIG. 8), respectively, of vertebrae V. Saddle 96 is selectively and freely translatable along arcuate path S relative to receiver 32 in sagittal planes SP1 and SP2 (FIG. 9), respectively, of vertebrae V.

According to the orientation and position of sections 134, 136 of each rod 108, bone fasteners 30 are each moved to a second configuration such that each implant cavity 106 of receiver 32 is selectively rotatable relative to shaft 52 within transverse planes TP1 and TP2. Implant cavity 106 is relatively rotatable about transverse axis t such that receiver 32 rotates through an angular range α (FIGS. 1 and 3) relative to axis $a_1$. This configuration allows orientation of implant cavity 106 to receive each of sections 134, 136 such that receivers 32 can capture rods 108. Saddle 96 translates relative to carrier 46 along path S and is rotatable about second axis $a_2$ through an angular range β in sagittal planes SP1 and SP2 to receive and accommodate the orientation and position of sections 134, 136.

In the second configuration, first setscrews 42 are threaded into the threaded portion of inner surface 38 of receiver 32 to advance distal faces 84 of first setscrews 42 into engagement with proximal faces 80, 82 of carriers 46 such that carriers 46 apply a first force and engage shafts 52, as described above. Second setscrews 118 are then threaded into the threaded portion of inner surface 114 of first setscrew 42 to advance tip 130 into engagement with rod 108 disposed in implant cavity 106 such that rod. 108 engages second concave surface 104 of saddle 96. This configuration causes a compressive force between saddle 96 and carrier 46 thereby locking the orientation of saddle 96 relative to arcuate path S. This configuration also applies a second force to shaft 52 through carrier 46. The second force is transmitted through saddle 96 to carrier 46 causing interference surfaces 72, 74 of carrier 46 to engage interference surfaces 68, 70 of shaft 52, as described above. This configuration fixes bone fastener 30 in an orientation of shaft 52 to prevent receiver 32 from moving relative to shaft 52 and fix bone fastener 30 in an orientation to receive and accommodate the orientation and position of sections 134, 136.

In one embodiment, as shown in FIGS. 3 and 7, first end 58 of shaft 52 includes a longitudinal cavity 138 extending distally from cavity 50 along first longitudinal axis $a_1$. Bone screw pocket 138 is configured for disposal of a biasing member, such as, for example, a silicone member or a spring that applies a resilient force to receiver 32 to maintain a force applied to bone fastener 30.

Bone fastener 30 may be employed as a bone screw, pedicle screw or multi-axial screw used in spinal surgery. In one embodiment, the spinal implant system includes an agent, which may be disposed, packed or layered within, on or about the surfaces of bone fastener 30. It is envisioned that the agent may include bone growth promoting material, such as, for example, bone graft to enhance fixation of the fixation elements with vertebrae.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of the spinal implant system can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair spinal deterioration or damage, with the aid of the spinal implant system. Upon completion of a procedure employing the spinal implant system described above, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
a proximal portion including an inner surface that defines a cavity;
a carrier disposed in fixed engagement with the inner surface and including at least one arm defining a proximal face, the at least one arm having a lateral opening;
a pivoting member being disposed with the carrier and relatively moveable therefrom, the pivoting member defining an implant cavity with the proximal portion, the pivoting member having at least one projection that extends through the lateral opening;
a distal portion defining a longitudinal axis and being configured to penetrate tissue; and
a first coupling member,
wherein the proximal portion is rotatable relative to the distal portion in a first plane of a body and the pivoting member is rotatable relative to the proximal portion in a second plane of the body, and the first coupling member is engageable with the proximal face such that the carrier engages the distal portion to fix the bone fastener in an orientation.

2. A bone fastener as recited in claim 1, wherein the at least one arm comprises a pair of spaced apart arms each defining a proximal face.

3. A bone fastener as recited in claim 1, wherein the first coupling member includes an inner surface that defines a longitudinal passageway, and further comprising a second coupling member disposed within the longitudinal passageway.

4. A bone fastener as recited in claim 3, wherein the first and second coupling members are coaxial.

5. A bone fastener as recited in claim 3, wherein the second coupling member comprises a tip configured to engage the implant disposed within the implant cavity.

6. A bone fastener as recited in claim 3, wherein the second coupling member is engageable with the first coupling member in rotation to effect axial translation of the second coupling member such that rotation of the second coupling member advances the second coupling member distally along the longitudinal axis and into engagement with the implant.

7. A bone fastener as recited in claim 1, wherein the first coupling member is engageable with the inner surface in rotation to effect axial translation of the first coupling member such that rotation of the first coupling member advances the first coupling member distally along the longitudinal axis and into engagement with the proximal face.

8. A bone fastener as recited in claim 1, wherein the proximal face is planar.

9. A bone fastener as recited in claim 1, wherein the pivoting member is configured for translation relative to the carrier along an arcuate path.

10. A bone fastener as recited in claim 1, wherein the carrier extends beyond the proximal portion to overlap the distal portion.

11. A bone fastener as recited in claim 1, wherein the carrier includes an interference surface that extends beyond the proximal portion to engage an interference surface of the distal portion.

12. A bone fastener as recited in claim 1, further comprising a transverse pin, wherein the distal portion defines a longitudinal cavity configured for disposal of the proximal portion and the pin extends through the proximal portion and the distal portion to retain the proximal portion with the distal portion.

13. A bone fastener as recited in claim 1, wherein the proximal portion is rotatable in a range of approximately 0 to 60 degrees relative to the distal portion.

14. A bone fastener as recited in claim 1, wherein the pivoting member is rotatable in a range of approximately 0 to 30 degrees relative to the proximal portion.

15. A bone fastener as recited in claim 1, wherein the proximal portion is selectively rotatable to an angular orientation in a range of approximately 0 to 60 degrees relative to the distal portion within the first plane.

16. A bone fastener as recited in claim 1, wherein the pivoting member is selectively rotatable to an angular orientation in a range of approximately 0 to 30 degrees relative to the proximal portion within the second plane.

17. A spinal implant system comprising:
at least one bone fastener comprising:
a receiver defining a first longitudinal axis and including spaced apart arms that include an inner surface of the receiver, the receiver further including an extension,
a carrier including a first surface disposed in fixed engagement with the inner surface, a second concave surface defining a first lateral opening and a second lateral opening and a pair of spaced apart arms each defining a proximal face, a saddle defining a first surface configured for slidable engagement with the second surface of the carrier along an arcuate path and a second concave surface that defines an implant cavity with the receiver, the implant cavity defining a second axis transverse to the first longitudinal axis and being configured for disposal of an implant, the saddle including a first arm that extends through the first lateral opening and a second arm that extends through the second lateral opening, the first and second arms being engageable with the carrier to limit movement of the saddle, a tissue penetrating shaft extending between a first end and a second end, the first end including a cavity configured for disposal of the extension;

a first setscrew rotatable relative to the receiver and engageable with the inner surface for axial translation relative to the receiver, the first setscrew including a distal face configured to engage the proximal face of the carrier and an inner surface that defines a longitudinal passageway;

a second setscrew rotatable relative to the first setscrew and engageable with the inner surface of the first setscrew for axial translation relative to the first setscrew, the second setscrew including a tip, and a vertebral rod configured for disposal within the implant cavity, wherein the bone fastener is movable between a first configuration such that the receiver is selectively rotatable relative to the shaft in a transverse plane of a body and the saddle is selectively rotatable relative to the receiver in a sagittal plane of the body, and a second configuration such that the first setscrew is rotatable to advance the distal face into engagement with the proximal face of each of the pair of spaced apart arms such that the carrier applies a first force and engages the shaft and the second setscrew is rotatable to advance the tip into engagement with the rod and the rod engages the concave surface of the saddle to apply a second force to the shaft through the carrier such that the application of the forces and engagement of the carrier with the shaft fixes the bone fastener in an orientation.

18. A method for treating a spine disorder, the method comprising the steps of:

providing a bone fastener comprising:
a proximal portion including an inner surface that defines a cavity,
a carrier disposed in fixed engagement with the inner surface and including at least one arm defining a proximal face, the at least one arm having a lateral opening,
a pivoting member being disposed with the carrier and relatively moveable therefrom, the pivoting member defining an implant cavity with the proximal portion, the pivoting member having at least one projection that extends through the lateral opening,
a distal portion defining a longitudinal axis and being configured to penetrate tissue, and
a first coupling member;

attaching the distal portion with vertebrae;

providing a vertebral rod disposed in an orientation;

selectively rotating the proximal portion relative to the distal portion in a first plane of a body, and selectively rotating the pivoting member relative to the proximal portion in a second plane of the body, to the orientation to dispose the rod in the implant cavity; and engaging the first coupling member with the proximal face such that the carrier engages the distal portion to prevent movement of the proximal portion relative to the distal portion.

19. A method as recited in claim 18, wherein the step of providing a bone fastener comprises the first coupling member having an inner surface that defines a longitudinal passageway and the bone fastener further comprises a second coupling member disposed within the longitudinal passageway; and further comprising the step of engaging the engaging the second coupling member with the rod to further prevent movement of the proximal portion relative to the distal portion.

20. A method as recited in claim 18, wherein the step of engaging the first coupling member with the proximal face comprises rotating the first coupling member such that the first coupling member is advanced distally along the longitudinal axis to apply a first force to the carrier such that the carrier engages the distal portion, and the step of engaging the second coupling member with the rod comprises rotating the second coupling member such that the second coupling member is advanced distally along the longitudinal axis through the longitudinal passageway to apply a second force to the distal portion, wherein the application of the forces and engagement of the carrier with the distal portion prevent movement of the proximal portion relative to the distal portion.

* * * * *